United States Patent [19]

Schuman

[11] Patent Number: 5,607,420
[45] Date of Patent: Mar. 4, 1997

[54] SURGICAL TOOL FOR USE WITH A CONTACT LASER

[75] Inventor: Daniel Schuman, Boca Raton, Fla.

[73] Assignee: Surgical Laser Technologies, Inc., Oaks, Pa.

[21] Appl. No.: 88,247

[22] Filed: Jul. 7, 1993

Related U.S. Application Data

[63] Continuation-in-part of Ser. No. 841,053, Feb. 5, 1992, abandoned.

[51] Int. Cl.[6] ................................................. A61B 17/00
[52] U.S. Cl. ................................. 606/15; 606/2; 606/17; 606/28; 604/20
[58] Field of Search .......................... 606/28, 31, 27, 606/2–18; 607/89; 128/4, 6; 604/902, 118, 19, 20, 119

[56] References Cited

U.S. PATENT DOCUMENTS

| | | | |
|---|---|---|---|
| 3,982,541 | 9/1976 | L'Esperance, Jr. | 606/4 |
| 4,146,019 | 3/1979 | Bass et al. | 128/6 |
| 4,207,874 | 6/1980 | Choy | 128/6 |
| 4,313,431 | 2/1982 | Frank | 128/7 |
| 4,418,688 | 12/1983 | Loeb | 128/6 |
| 4,419,987 | 12/1983 | Ogiu | 128/4 |
| 4,445,517 | 5/1984 | Feild | 604/118 |
| 4,592,353 | 6/1986 | Daikuzono | 606/17 |
| 4,646,737 | 3/1987 | Hussein et al. | 606/28 |
| 4,770,653 | 9/1988 | Shturman | 604/21 |
| 4,850,351 | 7/1989 | Herman et al. | 128/303.1 |
| 5,154,166 | 10/1992 | Chikama | 128/4 |

FOREIGN PATENT DOCUMENTS

| | | | |
|---|---|---|---|
| 2147209 | 5/1985 | United Kingdom | 606/16 |

Primary Examiner—David M. Shay
Attorney, Agent, or Firm—Seidel, Gonda, Lavorgna & Monaco, P.C.

[57] ABSTRACT

The surgical tool is used in conjunction with a direct contact laser that is powered through a small diameter laser power tube. In one embodiment, the tool includes a bendable, rigid tube having a lumen sufficiently larger than the laser power tube such that upon application of an axial, inboard directed force, the laser power tube is axially compressed within the lumen of the bendable tube. The contact laser tip, located at the end of the power tube, is powered by a laser core which is retained within the lumen of the laser power tube. The laser core is flooded by irrigation and cooling fluid flowing through the laser power tube. This fluid is ejected or emitted from the distal end of the laser power tube immediately behind the laser contact tip. In one embodiment, the bendable tube includes a handle and a bendable, rigid nozzle made of plastic. A longitudinally actuated suction control valve is disposed in the handle. The laser power tube extends through the valve seat of this control valve such that upon actuation of the valve, the laser power tube and hence the contact laser tip moves with respect to the rigid tube.

6 Claims, 4 Drawing Sheets

SURGICAL TOOL FOR USE WITH A CONTACT LASER

This is a continuation-in-part of U.S. patent application Ser. No. 841,053, filed Feb. 25, 1992, now abandoned.

BACKGROUND OF THE INVENTION

The present invention relates to a surgical tool which is used in conjunction with a contact laser.

Direct contact lasers, such as neodymium:yttrium-aluminum-garnet (ND:YAG) contact lasers, have been found useful in sinus surgery, head and neck surgery (otolaryngology), oral surgery, tracheobronchial surgery, tonsillectomies, bronchoscopic, cystoscopic and gastroscopic surgery. Also the contact laser may be useful in conjunction with other types of endoscopic or microscopic surgical procedures. KTP or potassium titanyl phosphate lasers are ND:YAG lasers that use a crystal of KTP at their output. Direct contact lasers differ from radiation emitting lasers in that contact probes (the laser crystals attached to the end of the laser core) work only when in direct contact with the tissue or medium at the surgical site. Contact lasers use thermal energy rather than laser light to remove, cut or cauterize a surgical site. Direct contact laser surgery provides the surgeon with tactile feedback or stimulation during the surgical procedure. This enhances the surgical technique and reduces the learning curve associated therewith.

U.S. Pat. No. 4,146,019 to Bass discloses a glass fiber laser core encased in a sheath. An irrigation fluid line is attached to the laser core sheath and extends beyond the distal end of the laser core. A laser crystal is affixed to the distal end of the laser core and is covered by an end cap. The end cap defines a window which is washed by irrigation fluid supplied by the irrigation fluid line attached to the sheath of the laser core. The laser disclosed in the Bass patent disclosure is not a direct contact, thermal surgical laser tip. The Bass laser emits laser light which irradiates the surgical site. The encased laser core and the attached irrigation fluid line are loosely contained in the lumen of a significantly larger outer tube. In addition to the laser core, six other lines (fiber optic lines, irrigation and suction lines) are loosely contained in the lumen of the large outer tube. Even though the laser core can move laterally in the larger outer tube, Bass does not disclose the use of a direct contact laser because the attached irrigation fluid line protrudes beyond the distal end of the laser core and end cap. In contact laser surgery, the surface of the contact laser tip must be completely exposed such that the surgeon can place the tip on the surgical site.

U.S. Pat. No. 5,154,166 to Chikama discloses a disposable endoscope cover. U.S. Pat. No. 4,770,653 to Shturman discloses a device having a laser core which terminates at a distal end of a long, hollow rod. The laser core does not move beyond the distal end of the rod. Shturman also shows a radiation transparent end cap which is attached to the end of the laser core. Shturman further discloses a rigid positioning body containing the laser crystal which can move axially within a hollow conduit by a translational force applied to a guide wire attached to the body. However, the Shturman laser is not a direct contact, thermal laser. Shturman specifically discusses the emission of laser radiation from the laser crystal at the distal end of the optical fiber.

U.S. Pat. No. 4,419,987 to Ogiu discloses a laser endoscope having a disc shaped glass cover at the distal end of a laser core guide. Ogiu specifically relates to laser beams emitted from a laser source through the laser guide. Ogiu does not show, teach or suggest the use of a direct contact, thermal laser tip. U.S. Pat. No. 4,418,688 to Loeb discloses a microcatheter having a directable, light emitting laser. Cables running through a collar near the distal end of the conduit enable the upper or lower angular adjustment of a laser affixed to a laser power core. Loeb further discusses a lens which focuses the laser light at a specific location. Loeb does not show, teach or suggest the use of a direct contact, thermal surgical laser tip. U.S. Pat. No. 4,207,874 to Choy discloses a laser tunneling device which uses a laser to irradiate an item.

U.S. Pat. No. 4,850,351 to Herman discloses a wire guided laser catheter having longitudinal channels formed in the lumen of a conduit. The channels carry waveguides, such as optical fibers, and these optical fibers are adapted to transmit laser light. The optical fibers are not secured within the channels and are permitted to longitudinally move within the channel as the catheter conduit is bent. The distal ends of the optical fibers are secured at the distal portion of the catheter conduit. The fibers are secured to an optically transparent distal end cap which is formed from an optical glass which emits the radiant energy of the laser.

U.S. Pat. No. 4,313,431 to Frank discloses an endoscope apparatus with a laser light conductor. Frank provides that a tumor is irradiated with light emitted from a conventional laser passing through a light conductor. The light conductor is slidably guided by a spring loaded push wire extending through a pipe. The laser crystal at the end of the light conductor moves beyond the distal end of the pipe based upon the longitudinal movement of the push wire. The push wire is rearwardly biased thereby resisting forward axial movement of the laser crystal. However, Frank discloses the use of an irradiating laser tip and not a direct contact laser crystal tip.

OBJECTS OF THE INVENTION

It is an object of the present invention to provide a surgical tool that is used in combination with a contact laser, wherein the laser is inserted through a lumen of a bendable, rigid tube and wherein the contact laser tip extends from the distal end of the tube.

It is another object of the present invention to provide a surgical tool wherein the lumen of the bendable tube is large enough such that the laser and the laser power cord is axially compressed with the lumen upon application of an axially aligned, inboard directed force, thereby enabling the surgeon to delicately sear or remove by thermal surgical techniques, the object at the surgical site.

It is a further object of the present invention to provide a surgical tool that controllably provides suction of fluid and debris from the operating field through the lumen of the bendable tube.

It is another object of the present invention to provide a surgical tool wherein the direct contact surgical laser tip, coupled to a laser power tube, is forwardly biased such that the direct contact laser tip is rearwardly depressible upon contact at the surgical site.

It is a further object of the present invention to mount and spring load a laser power tube, carrying a direct contact laser tip at its distal end, in a conduit such that the surgeon can palpate the tip at the surgical site.

It is another object of the present invention to provide a conduit, loosely retaining the laser power tube therein, with a handle and further to include an operator suction control valve on the handle.

It is an additional object of the present invention to provide an operator suction control valve that is longitudinally actuated and wherein the longitudinally actuated valve is coupled to the laser power tube such that the operator can move or translate the direct contact laser tip by longitudinally moving the valve control.

BRIEF DESCRIPTION OF THE DRAWINGS

Further objects and advantages of the present invention can be found in the detailed description of the preferred embodiments when taken in conjunction with the accompanying drawings in which.

SUMMARY OF THE INVENTION

The surgical tool is used in conjunction with a direct contact laser that is powered through a small diameter laser power tube. In one embodiment, the tool includes a bendable, rigid tube having a lumen sufficiently larger than the laser power tube such that upon application of an axial, inboard directed force, the laser power tube is axially compressed within the lumen of the bendable tube. The contact laser tip, located at the end of the power tube, is powered by a laser core which is retained within the lumen of the laser power tube. The laser core is flooded by irrigation and cooling fluid flowing through the laser power tube. This fluid is ejected or emitted from the distal end of the laser power tube immediately behind the laser contact tip. In one embodiment, the bendable tube includes a handle and a bendable, rigid nozzle made of plastic. A longitudinally actuated suction control valve is disposed in the handle. The laser power tube extends through the valve seat of this control valve such that upon actuation of the valve, the laser power tube and hence the contact laser tip moves with respect to the rigid tube.

DETAILED DESCRIPTION OF THE PREFERRED EMBODIMENTS

Figure 1:
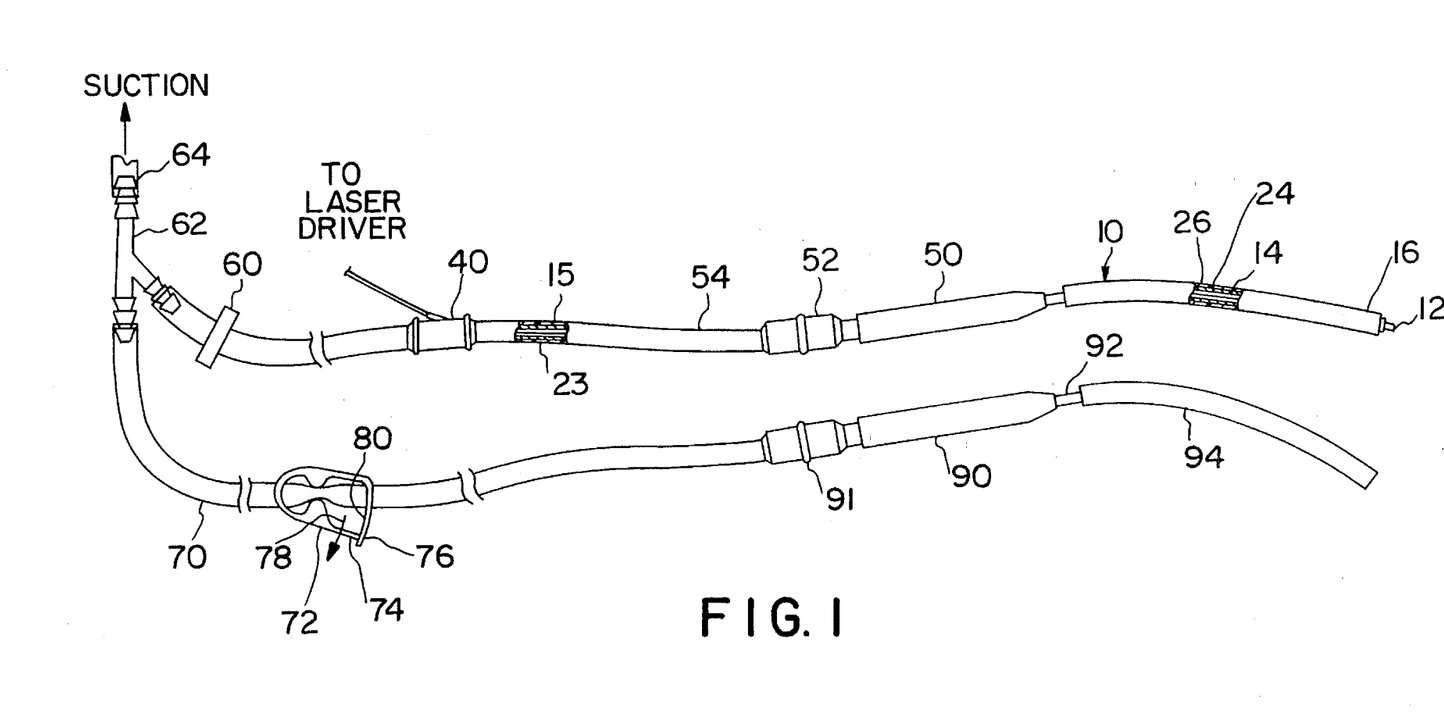
FIG. 1 illustrates a surgical tool in accordance with the principles of the present invention and which is used in combination with a laser and a laser power tube.
Figure 2:
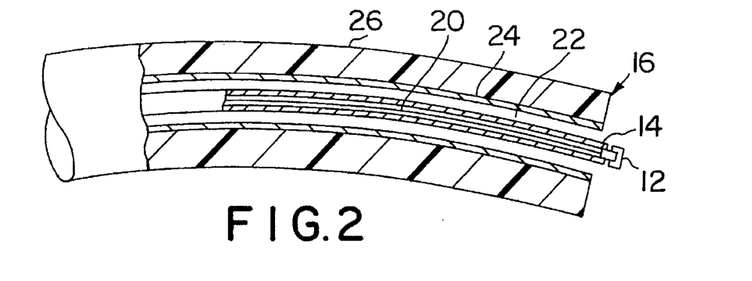
FIG. 2 illustrates an enlarged, cross-sectional view of the distal end of the rigid, bendable tube loosely retaining the laser power tube therein and illustrating a laser contact tip protruding from the distal end thereof.

The present invention relates to surgical tools for direct contact laser surgery. FIG. 1 shows a surgical tool used in conjunction with a laser. In this embodiment, the laser is a consumable tip laser having a tip 12 that is detachably connected to a laser power tube 14. FIG. 2 is an enlarged, cross-sectional view of the distal end 16 of tool 10. The consumable or direct contact laser tip 12 is screwed onto laser power tube 14. In this embodiment, the outside casing of laser power tube 14 is made of a plastic or polymer and a laser feed or core 20 is inserted in the lumen of laser power tube 14. An irrigation fluid flows through the lumen of laser power tube 14 in order to cool power core 20 and irrigate the operating field. This fluid is ejected from tube 14 slightly behind tip 12. In a working embodiment, a YAG laser is utilized. The contact YAG laser is manufactured by many manufacturers, including SLT. In a working embodiment, laser power tube 14 has a 2 millimeter diameter whereas laser power core 20 has a 0.6 millimeter diameter. Tip 12 has substantially the same diameter as laser power tube 14. Since blood vessels may be sized up to 2 millimeters in diameter, the size and adaptability of the surgical tools used in microscopic laser surgery are important.

Figure 3:
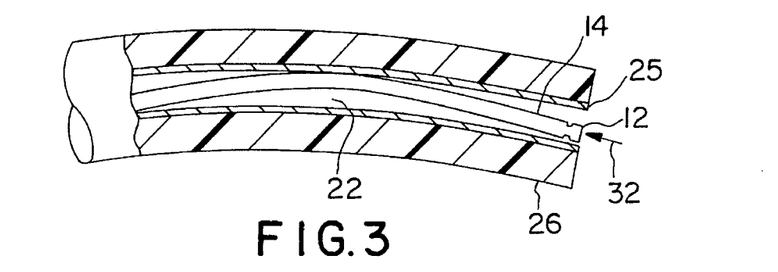
FIG. 3 illustrates an enlarged, cross-sectional view of the tube as shown in FIG. 2 wherein the laser power tube is axially compressed within the rigid, bendable tube.
Figure 4:
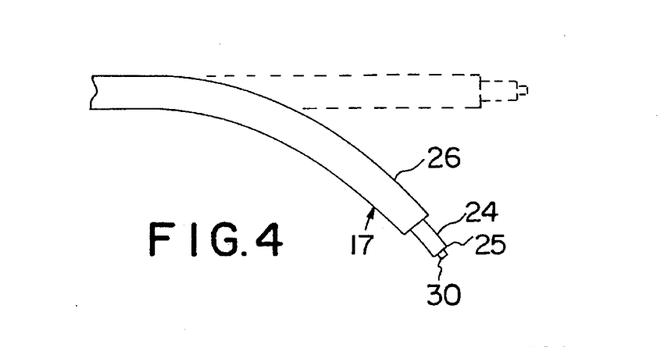
FIG. 4 diagrammatically illustrates the distal end of the rigid tube with a soft touch casing axially and longitudinally moved to expose the end of the rigid tube and which further illustrates how the rigid tube can be bent.

Laser power tube 14 is loosely disposed or retained in lumen 22 of a bendable, rigid tube 24. In a working embodiment, bendable, rigid tube 24 is made of metal. Lumen 22 is approximately 3.5 millimeters in diameter. An axially movable, soft touch casing 26 surrounds bendable tube 24. Irrigation fluid is supplied through the lumen of power tube 14 and is generally ejected at or near the point of attachment of laser tip 12 with power tube 14. See. FIG. 2. Fluid and debris are suctioned from the operating field via lumen 22 of bendable tube 24. As shown in FIG. 4, distal end 16 of surgical tool 10 can be bent by the surgeon such that the tube, as well as the loosely retained laser tip and laser power tube, can be placed at specific locations in the body cavity of a patient during the microscopic surgery. As also shown in FIG. 4, soft touch casing 26 can be axially moved to expose the end 25 of bendable tube 24. In FIG. 3, tube end 25 is covered by casing 26 thereby substantially eliminating a sharp tube end which may present a problem during microscopic surgical procedures. Alternatively, an exposed tube end 25 as shown in FIG. 4 may, at times, be beneficial during microscopic surgery. Specifically, the exposed end may be used to scrape the surgical site. The distal end region 30 of the consumable tip laser 12 and laser tube 14 is shown as protruding from tube 24 in FIG. 4. The dashed lines in FIG. 4 represent distal end region 17 being straightened as compared with the curved distal end region 17 shown in solid lines in that figure.

FIG. 3 shows that laser power tube 14 and hence consumable or contact laser tip 12 can axially warp and be axially compressed within lumen 22 upon application of an axially aligned inboard directed forced shown by arrow 32 in FIG. 3. This feature of the present invention enables the surgeon to delicately conduct laser microsurgery on soft tissue without damaging the harder tissue surrounding the object being surgically removed or altered. As shown in FIG. 1, laser tube 14 longitudinally extends a relatively large distance within lumen 22 (FIG. 2). FIG. 1 also shows proximal lumen region 23 and proximal laser power tube portion 15. In a working embodiment, bendable metal tube 24 is approximately 14 centimeters in length and the soft touch, axially movable casing 26 is approximately 12.5 centimeters in length. Accordingly, the soft touch casing extends over substantially all of the bendable metal tube 24. The soft touch casing enables the surgeon to insert this surgical tool into the body cavity without damage to the surrounding tissue.

When activated, the consumable or contact tip laser generates heat. The tip, when hot, heats the surrounding fluid. Typically, this is irrigation fluid. This hot fluid and the hot contact tip of the laser are used by the surgeon to remove items at the surgical site. Since the tip becomes hot and bendable metal tube 24 conducts heat, the soft touch casing, which is made of a soft, resilient, rubber-like or insulative plastic, limits the distribution of heat to the surrounding tissue. The surgeon may find this helpful during the surgical procedure. If the surgeon desires to utilize the hot tube during the microscopic surgery, soft touch casing 26 can be axially moved to expose the end 25 of bendable metal tube 24, as shown in FIG. 4. This exposure may enable the surgeon to scrape the surgical site with the end of the tube or to utilize the locally generated hot fluid or the thermally excited contact laser tip to assist in the removal of objects from the body cavity. The hot irrigation fluid, delivered to the site from the laser power tube, can be used to "steam" or controllably remove objects at the surgical site.

In a working embodiment, the distance between distal end region 16 of tool 10 and laser power tube insertion port 40 in FIG. 1 is approximately 40 centimeters. Accordingly, if an axially directed inboard force is applied to laser tip 12 (see FIG. 3, force vector 32), laser power tube 14 warps within lumen 22 along the length of the lumen between the laser tip and insertion port 40 thereby permitting reasonably significant axial compression of the laser power tube within the lumen. In a working embodiment, an axial compression of approximately 3 millimeters has been noted.

The surgeon or operator can palpate the surgical site with the contact laser tip without significant difficulty. From a mechanical standpoint, the tip is generally spring loaded due to the compressibility of the power tube in the lumen of the rigid, outer tube. In a first, relaxed state, the power tube protrudes from the distal end of the outer tube. In an intermediate, active state, the laser tip contacts the surgical site which causes the partial axial compression of the power laser tube in the outer tube. This partial axial compression essentially spring loads the power tube and hence the tip against the surgical site. In an advanced, intermediate state, the spring loading of the contact laser increases at the surgical site due to the further compression of the power tube in the outer tube. In a fully compressed state, the contact laser tip is fully compressed within the outer tube and may be captured within or aligned with the distal end of the outer tube. The final active state may occur at low levels of spring loading on the surgical site (equivalent to a small degree of axial compression) or at higher levels of loading (equivalent to a large axial compression). The degree of spring load in the final active state depends upon the initial physical conditions such as the size of the lumen of the outer tube, the diameter of the laser power tube, the compressible length of power tube retained by the outer tube and the initial length of power tube protruding from the distal end of the outer tube.

At its proximal end, bendable tube 24 is surrounded by a handle 50. The handle is formed, in a working embodiment, in a rectilinear shape. Handle 50 also includes a hole linking the lumen of tube 24 with the ambient environment. By closing the hole, the surgeon increases the degree of suction at end 25 of tube 24. By opening the hole to the ambient environment, the degree of suction at the distal end of the tube is decreased since air is suctioned through the hole in the handle. Coupler 52 attaches a further coupling tube 54 to the base of the handle. Tube 24 extends through the handle but the handle portion of the tube is not bendable. Insertion port 40 is positioned in the coupling tube and permits insertion of laser power tube 14 into the lumen of coupling tube 54 as well as lumen 22 of bendable tube 24. Insertion port 40 is fluidly sealed to limit leakage of fluid and debris passing through coupling tube 54 due to the suction therethrough. Port 40 may be pneumatically sealed to provide good suction control through tubes 54 and 24. Conventionally, laser power tube 14 is coupled to a laser driver, a suction source or sink and other electronics for driving the laser, particularly to drive and cool laser tip 12.

A suction control valve 60 is disposed on coupling tube 54. Beyond control valve 60 a branch coupler 62 is attached to tube 54. A suction pump or sump is coupled to one port 64 of branch coupler 62. Branch coupler 62 provides suction for the primary coupling tube 54 and a secondary coupling tube 70. Secondary coupling tube 70 is connected to the second branch of branch coupler 62. A control device 72 is disposed on secondary coupling tube 70. In one embodiment, flow control device 72 is manufactured by Halkey Roberts Corporation of St. Petersburg, Fla. and is a plastic crimp controller which, upon depression of lever or catch arm 74 (opposite force vector 78), pinches the coupling tube thereby prohibiting suction and flow of fluid and debris through that tube. When spring loaded arm 76 is moved away from catch arm 74, arm 74 moves outboard or away from the tube pinch point as shown by arrow 78 and suction is permitted through coupling tube 70. Upon depression of operating lever catch arm 74 in a direction opposite arrow 78, the control valve pinches coupling tube 70 while lever catch arm 74 locks into one of a plurality of catch ridges on the inboard side 80 of arm 76.

The secondary coupling tube 70 is removably connected to a handle 90, via detachable coupler 91, and ultimately to a bendable, rigid metal tube 92 having a soft touch casing 94 surrounding a substantial portion thereof and particularly the distal end of the metal tube. The secondary bendable, rigid tube 92 and casing 94 is substantially the same as primary tube 24 except that the primary tube loosely retains the laser power tube therein. The soft casing on tube 92 may be axially moved to expose or cover the distal end of tube 92. Other tools can be attached to tube 70 via detachable coupler 92 by removal of handle 90 therefrom.

In operation, the surgeon using surgical tool 10 activates the laser while delivering irrigation fluid to the microscopic surgical field via power tube 14. Suction for the operating field is primarily provided by bendable tube 24. The surgeon changes the angular disposition of the tube by holding handle 50 and bending or manipulating the tube. The tube can be bent, the tube end can be exposed or covered by the soft-touch casing and the hot laser tip can be axially extended outward by insertion of additional lengths of power tube 14 into port 40. Tube 14 axially compresses within tube 24 upon application of an axially directed inboard force at tip 12. If tip 12 touches a bone or hard structure in the sinus or at a specific surgical site, the power tube 14 axially compresses within lumen 27. As stated earlier, tip 12 is a contact laser tip which generates heat. Since the microscopic surgical field is irrigated, the irrigation fluid is heated by the laser tip. Also as stated earlier, the surgeon uses the locally generated heat from the laser to assist in the removal of objects. During that time, control valve 72 on secondary coupling tube 70 may be closed thereby eliminating or reducing suction through the secondary surgical tool. If the surgeon desires to clean the operating field and not use the laser tool, the surgeon closes control valve 60 on primary tube 54, removes the primary surgical tool (bendable tube 24 and soft touch casing 26) from the body cavity, inserts the secondary surgical tool (bendable tube 92 and soft touch casing 94), opens secondary branch control valve 72, thereby permitting suction through the secondary branch coupling tube 70 as well as the secondary endoscopic surgical tool.

Figure 5:
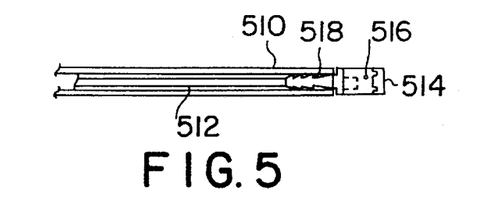
FIG. 5 diagrammatically illustrates the distal end region of the laser power tube, the contact laser crystal tip, and the small diameter laser core extending through the laser power tube.

FIG. 5 diagrammatically illustrates the distal end of laser power tube 510. The small diameter laser power tube carries, within its lumen, a laser power core 512. Laser power core 512 carries light radiation that is ultimately fed to direct contact laser tip 514. Laser power tip 514 may be part of the ND:YAG laser. Irrigating and cooling fluid is carried by power tube 510 and this fluid surrounds laser power core 512. Ultimately this fluid is ejected or emitted near the distal end of the laser power tube 510 via peripheral output ports, one of which is output port 516. The laser power core 512 is mounted in laser power tube 510 with an interference fit coupling 518. Irrigation fluid surrounding laser power core 512 flows past coupling 518 to cool the proximal end of contact tip 514.

Figure 6:
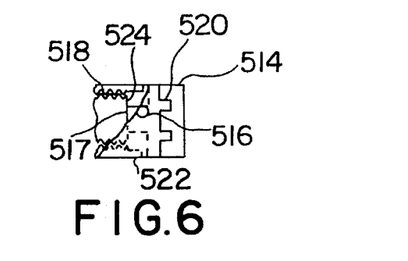
FIG. 6 diagrammatically illustrates the contact laser tip and coupler for the core.

FIG. 6 diagrammatically illustrates contact laser tip 514 which is gripped by fingers, one of which is finger 520, extending from casing 522. The proximal end 517 of contact tip 514 is thought to be in direct contact with the end of laser power core 512. Casing 522 is threadably attached to the distal end 524 of coupling 518. The cooling, irrigation fluid is ejected from casing 522 via peripheral ports, one of which is port 516.

Figure 7:
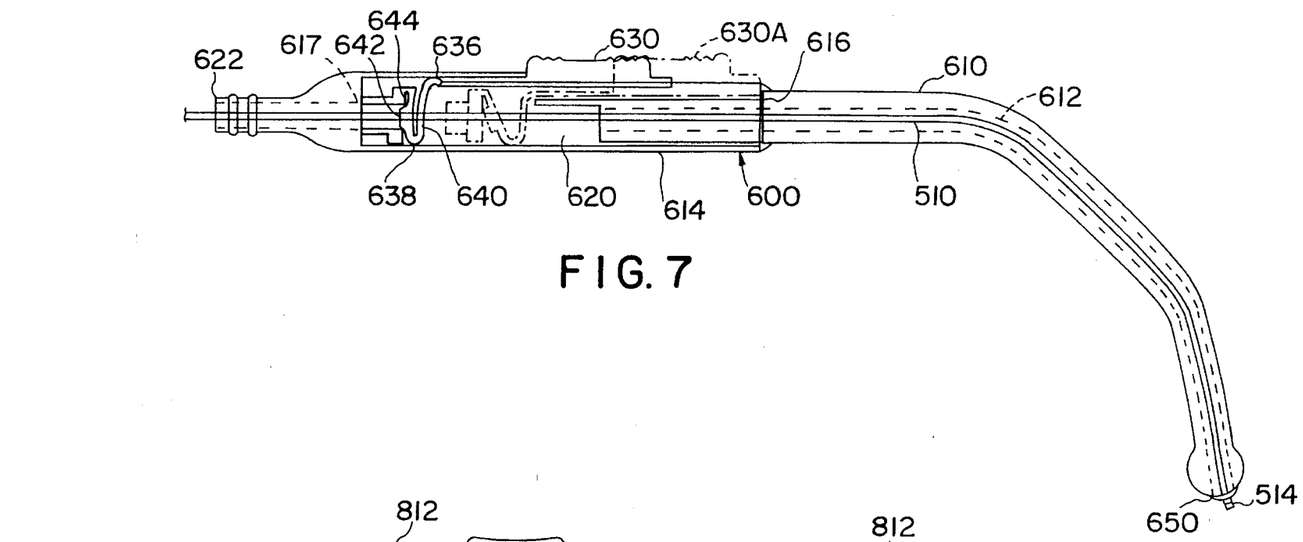
FIG. 7 diagrammatically illustrates another embodiment of the bendable tube which carries the laser power tube and further includes a longitudinally actuated suction control valve.
Figure 9:
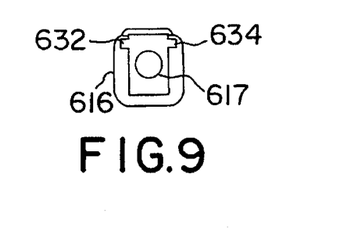
FIG. 9 diagrammatically illustrates a cross-sectional portion of the handle of the surgical tube.

FIG. 7 diagrammatically illustrates another embodiment of surgical tool 600. In this embodiment, surgical tool 600 includes a plastic, bendable, elongated nozzle tube 610 having a lumen 612 through which extends laser power tube 510. A contact laser tip 514 is attached to the distal end of laser power tube 510. A plastic handle 614 is attached to the proximal end 616 of bendable nozzle 610. Handle 616 has a generally rectangular cross-sectional shape as shown in FIG. 9. Also, handle 616 is hollow such that a suction can be drawn through its hollow body portion 620. Laser power tube 510 extends through the length of handle 616 and protrudes from the proximal end 622 of the handle. The proximal end of the handle attaches to a suction line. See FIG. 1.

Handle 616 includes an operator actuated, suction control valve which further includes a slidable control 630. FIG. 7 shows the slidable control valve in a rearward, closed position (with solid lines) and in a forward, open valve position (with dashed lines). The open valve is referenced as 630A. Slidable control valve 630 slides within longitudinally extending, laterally opposed channels 632 and 634 that are illustrated in FIG. 9. An S-shaped valve flap assembly 638 is movably disposed at the proximal end 636 of slide control valve 630. Valve assembly 638 includes an actuator flap panel 640, a valve stop flap 642, and a valve seat 644. Actuator flap panel 640, valve stop flap 642 and valve seat structure 644 are movable within the hollow body portion 620 of handle 616. The proximal end of valve seat structure 644 abuts internal, cylindrical port 617 of the handle when the valve is closed.

Figure 8:
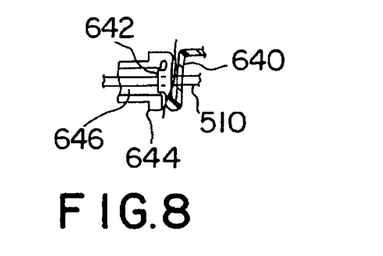
FIG. 8 diagrammatically illustrates the laser power tube extending through certain portions of the suction control valve.

Valve seat portion 644, as shown in FIG. 8, includes a proximal, generally cylindrical passage 646 which is closed by the rearward abutment of valve stop 642. When slide control valve 630 is in its distal or forward position (see control valve 630A), actuator flap 640 is angularly spaced from the valve stop flap 642 which is, in turn, angularly spaced from the valve seat 644. Further, the entire assembly 638 has moved from a proximal position in the handle to a distal position. In this position, the valve permits suction and fluid flow from the distal end of the handle to the proximal end 622 of the handle past the assembly itself and through passage 646 and port 617. When the operator control is in its rearward or proximal region, actuator flap 640 bears against the distal surface of valve stop flap 642 which flap, in turn, bears against valve seat 644.

The suction control, handle and nozzle is known in the art and is sold by Duval Corporation. However, this surgical tool operates solely as a suctioning device.

The present invention modifies this device by the insertion of laser power tube 510 extending therethrough. Laser power tube 510 extends through actuator flap 640 and valve stop flap 642. The insertion of laser power tube 510 through flaps 640 and 642 can be accomplished by piercing the flaps and thereafter inserting the laser power tube. As shown in FIG. 8, the tube runs through cylindrical passage 646 of seat 644.

The operator, with the present surgical tool, can move the laser power tube 510 at the same time he or she controls the degree of suction at distal end 650 of nozzle 610. The present surgical tool enhances the surgeon's ability to position laser contact tip 514 at the surgical site. For macro positioning adjustments, additional lengths of the laser power tube are fed into the conduit. See FIG. 1. For micro or fine positioning adjustments, the operator uses the longitudinal valve control in the handle.

Figures 10A, 10B:
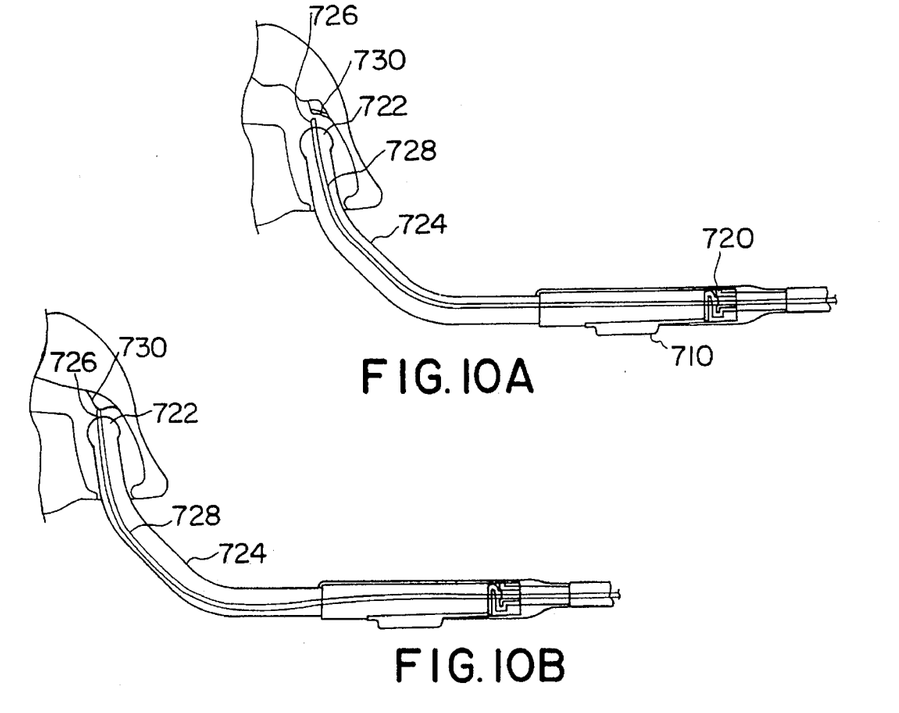
FIGS. 10A and 10B respectively diagrammatically illustrate the laser power tube in a relaxed mode and an axially compressed or spring loaded mode when the suction control valve is closed.

FIGS. 10A, 10B, 11A and 11B show various operating positions of the surgical tool. In FIG. 10A, operator control 710 is in a rearward or proximal position such that valve 720 is completely closed, thereby limiting or completely eliminating suction at distal end 722 of nozzle 724. The distal end 726 of the laser power tube 728 is very near surgical site 730. If the laser tip is actuated, the tip heats the irrigation fluid at the surgical site. This irrigation fluid is delivered to the site via the laser power tube. As shown in FIG. 10B, the surgeon can move distal end 722 by moving the entire surgical tool and, hence, move contact tip 726 into contact with surgical site 730. At that time, laser power tube 728 axially compresses within nozzle 724. By moving the surgical tool, the surgeon can palpate the contact tip 726 towards and away from surgical site 730. This feature enables the surgeon to palpate site 730 with controlled degrees of force against the tissue or obstruction at surgical site 730. Further, in both FIGS. 10A and 10B, irrigating and cooling fluid is being ejected from the distal end of laser power tube 728. Accordingly, surgical site 730 is being flooded with irrigation fluid. The temperature of this irrigation fluid is controlled by the surgeon with the heat generated by the laser tip. The thermal properties of this hot water assists in the removal of tissue and other obstructions at surgical site 730.

Figures 11A, 11B:
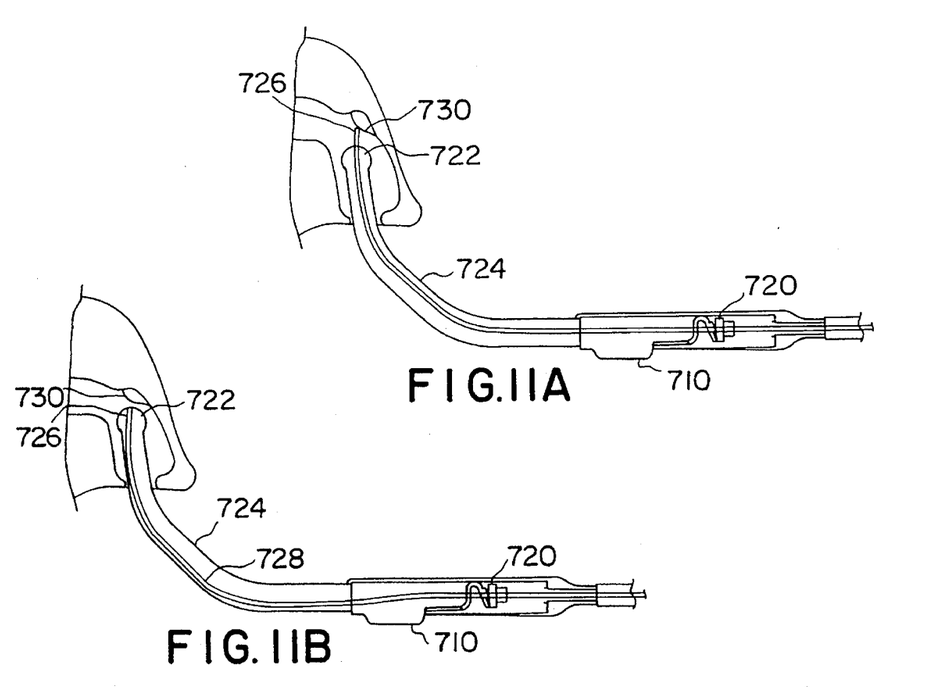
FIGS. 11A and 11B respectively diagrammatically illustrate palpation of the surgical site with the direct contact laser (similar to FIGS. 10A and 10B) with the suction control valve open (the palpation being accomplished by the axial compression of the laser power tube in the surgical tool)

In FIGS. 11A and 11B, operator control valve 10 is in a forward or distal position, such that suction valve 720 is completely open. A maximum degree of suction is established in nozzle 724 and at open distal end 722. In FIG. 11A, the contact laser tip 726 is placed on surgical site 730. In FIG. 11B, the surgeon has moved distal end 722 closer to surgical site 730 such that tip 726 is substantially aligned with distal end 722 of nozzle 724. The laser power tube 728 is axially compressed within nozzle 724. Simultaneously, suction control 710 is in its forward or distal position wherein valve 720 establishes the maximum degree of suction at surgical site 730.

It should be noted that an important operating feature of the present invention consists of a forward biased, but rearwardly depressible, contact laser tip (and also power tube) that enables a surgeon to apply a controlled force at the surgical site 730. It is the ability of the contact laser tip to be somewhat axially movable and rearwardly depressible based upon the degree of tip contact at the surgical site. The forward biasing can be accomplished by many mechanical devices, such as springs or hydraulic or other electronic devices or controls, for example, a solenoid, spring balanced control.

In combination with the direct contact laser tip, the small, but significant flow of cooling/irrigation fluid from the laser power tube combined with suction of the surgical tool enables the surgeon to have a device which fulfills several functions. The first function provides a laser driven surgical tool that can cut, cauterize, and scrape a surgical site. The second function enables the physician to irrigate the surgical site with the irrigation and coolant water from the laser power tube. The third operational characteristic is the ability of the surgeon to controllably suction the irrigation fluid from the surgical site. Not only does the present surgical tool enable the physician to control suction with a simple, longitudinally actuated hand control, but the surgeon can also position the laser contact tip at a particular surgical site. This control provides a greater degree of control over the positioning of the contact laser tip than is available with previous devices. Additionally, the surgeon can establish the degree of spring loaded force of the tip by altering certain physical parameters such as the protruding length of the power tube from the conduit.

It should be noted that the suction control can be configured with other types of valves. The longitudinally actuated, multiple flap valve disclosed herein simply incorporates the present embodiment of the invention.

Figure 12:
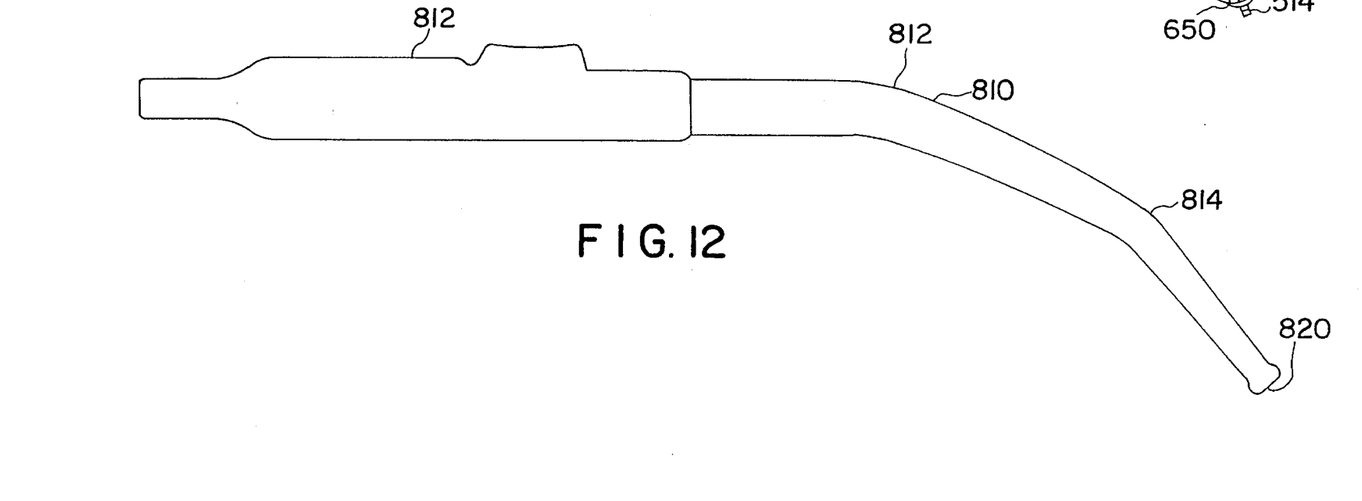
FIG. 12 diagrammatically illustrates the rigid, bendable tube before application of heat and conversion into the different angular disposition illustrated in FIG. 7.

FIG. 12 diagrammatically illustrates the shape of nozzle 810 and its relation to handle 812 prior to heating. Nozzle 810, which is made of plastic, can be heated by the application of hot air or hot water. After application of this heat, the nozzle can be bent from the position shown in FIG. 12 to the position shown in FIG. 7. It should be noted that the angular disposition of the nozzle has been changed. Also, due to the temperature sensitivity of the nozzle, the break points 812, 814 can be changed. Additionally, it has been discovered that nozzle 810 has memory in that, upon re-application of heat, the nozzle will return to its original configuration. If nozzle 810 was originally an elongated cylinder having a single axial center line, after the nozzle is heated and bent to a position such as that shown in FIG. 12 or FIG. 7, upon re-application of heat, that nozzle will return to its original cylindrical shape with a singular axial center line. The nozzle 810 in FIG. 12 has generally three axial center lines, one terminating at break point 812, the second terminating at break point 814, and the third extending from break point 814 through the distal end 820 of the nozzle.

The claims appended hereto are meant to cover modifications and changes within the spirit and scope of the present invention.

What is claimed is:

1. In combination with a thermal surgical laser that is powered through a small diameter combination laser power fiber optic and coolant carrying tube, a surgical tool coupled to a source of suction comprising:

a conduit, having a distal open end, establishing a suction line from a surgical site adjacent to said open end to said source of suction for removal of debris and fluids including irrigation fluid;

an elongated handle, defining a portion of said conduit, and a contiguous bendable, rigid tube defining a distal end portion of said conduit, said handle including a longitudinally actuated operator suction control valve, and a forward biased, rearwardly depressible heat generating surgical laser tip attached to a distal end of said laser power fiber optic, the surgical laser tip protruding from said distal open end of said conduit and adapted to palpate and contact said surgical site and to heat irrigation fluid for selectively searing or blanching of tissue and other obstructions, said laser power fiber optic and coolant carrying tube being movably affixed to said longitudinally actuated operator suction control valve such that upon actuation of said valve said surgical laser tip extends or retracts with respect to said distal open end of said bendable, rigid tube.

2. A surgical tool as claimed in claim 1 wherein said control valve includes a valve seat formed within said elongated handle and a stopper coupled to an operator slide control as said longitudinally actuated valve.

3. A surgical tool as claimed in claim 2 wherein said laser power fiber optic extends through said handle, said valve seat and said stopper.

4. In combination with a thermal surgical laser that is powered through a small diameter combination laser power fiber optic and coolant carrying tube, said tube receiving a laser power fiber optic having a distal end, a combination suction and surgical tool coupled to a source of suction comprising:

a hollow handpiece having a proximal end and a distal end, and including a longitudinally actuated operator suction control valve;

a bendable, rigid tube extending from said distal end of said handpiece, said rigid tube having an open end adapted to be placed adjacent to a surgical site and having a lumen therethrough sufficiently larger than said laser power fiber optic such that when a predetermined length of said laser power fiber optic is disposed in said lumen and a substantially axially aligned, inboard directed force is applied to said laser power fiber optic, said laser power fiber optic is given a degree of warp within said lumen and said fiber optic length is compressed therein;

a heat generating thermal surgical laser tip carried at the distal end of said laser power fiber optic for heating irrigation fluid for selectively searing or blanching of tissue and other obstructions, the degree of warp of said laser power fiber optic being sufficient to establish an axially rearward spring loading for said laser tip when the end of said laser power fiber optic protrudes beyond said open end of said rigid tube for the laser tip to palpate said surgical site; and, a coupling tube in communication with said source of suction, said handpiece and said bendable, rigid tube, such that suction is provided through said lumen and at said surgical site for removal of debris and fluids including irrigation fluids;

wherein said laser power fiber optic extends through at least a portion of said coupling tube, through said handpiece and said bendable, rigid tube, said laser power fiber optic and coolant carrying tube being movably affixed to said longitudinally actuated operator suction control valve such that upon actuation of said valve said surgical laser tip extends or retracts with respect to said distal open end of said bendable, rigid tube.

5. A surgical tool as claimed in claim 4 wherein said laser power fiber optic carries irrigation and cooling fluid and said laser tip includes a discharge port for said irrigation and cooling fluid.

6. A surgical tool as claimed in claim 4 wherein said control valve includes a valve seat formed within said handpiece and a stopper coupled to an operator slide control as said longitudinally actuated valve and said laser power fiber optic extends through said handle, said valve seat and said stopper.

* * * * *